United States Patent

Goto et al.

Patent Number: 5,654,257
Date of Patent: Aug. 5, 1997

[54] 1-CYCLOALKENYLTETRAZOLINONES

[75] Inventors: Toshio Goto, Kokubunji-machi; Yoshinori Kitagawa, Tochigi; Seishi Ito, Oyama; Katsuhiko Shibuya, Oyama; Tatsuya Yamaoka, Oyama; Chieko Ueno, Oyama; Yoshiko Kyo, Oyama, all of Japan

[73] Assignee: Nihon Bayer Agrochem K.K., Tokyo, Japan

[21] Appl. No.: 601,748

[22] Filed: Feb. 15, 1996

[30] Foreign Application Priority Data

Feb. 22, 1995  [JP]  Japan ..................... 7-058120

[51] Int. Cl.$^6$ ............... A01N 43/713; C07D 257/04
[52] U.S. Cl. ............... 504/261; 504/225; 504/235; 504/247; 504/249; 544/132; 544/366; 546/165; 546/210; 548/251
[58] Field of Search ............... 548/251; 546/210, 546/165; 544/132, 366; 504/225, 235, 247, 249, 261

[56] References Cited

U.S. PATENT DOCUMENTS

| | | |
|---|---|---|
| 4,618,365 | 10/1986 | Covey et al. |
| 4,826,529 | 5/1989 | Covey et al. |
| 4,830,661 | 5/1989 | Covey et al. |
| 5,003,075 | 3/1991 | Covey et al. |
| 5,019,152 | 5/1991 | Covey et al. |
| 5,342,954 | 8/1994 | Goto et al. |
| 5,344,814 | 9/1994 | Goto et al. |
| 5,347,009 | 9/1994 | Goto et al. |
| 5,347,010 | 9/1994 | Goto et al. |
| 5,362,704 | 11/1994 | Goto et al. |

FOREIGN PATENT DOCUMENTS

| | | |
|---|---|---|
| 0146279 | 11/1984 | European Pat. Off. |
| 0202929 | 11/1986 | European Pat. Off. |
| 0646577 | 4/1995 | European Pat. Off. |

OTHER PUBLICATIONS

Pestic. Sci. 1990, 30 pp. 259–274 (Synthesis and Structure . . . ).
(1987) Bristish Crop Protection Conference—Weeds pp. 249–255, Bell et al.

*Primary Examiner*—Jacqueline Haley
*Attorney, Agent, or Firm*—Sprung Horn Kramer & Woods

[57] ABSTRACT

1-cycloalkenyltetrazolinone derivatives of the following herbicidal formula

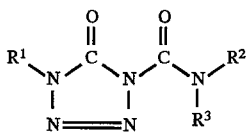

$R^1$ is cycloalkenyl which may optionally be substituted by halogen $C_{1-4}$ alkyl, or bicycloalkenyl which may optionally be substituted by halogen or $C_{1-4}$ alkyl, and $R^2$ and $R^3$ each independently is alkyl, cycloalkyl, phenyl (optionally substituted by a member selected from the group consisting of nitro, cyano, halogen, alkyl, haloalkyl, alkoxy, haloalkoxy and alkylthio), alkenyl and alkynyl, or $R^2$ and $R^3$ together with the N-atom to which they are bonded form, a 5- or 6-membered heterocyclic ring which may optionally contain a further hetero atom, said heterocyclic ring optionally being benzo-condensed, or a C-$_{1-4}$ alkyl, and intermediates therefore of the formula

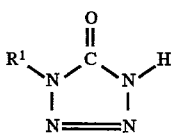

15 Claims, No Drawings

1-CYCLOALKENYLTETRAZOLINONES

The present invention relates to novel 1-cycloalkenyltetrazolinones, to a process for their preparation, and their use as herbicides, as well as to novel intermediates for their preparation and to processes for their preparation.

It has been already known that a certain kind of 1-substituted phenyl-tetrazolinone derivatives has herbicidal activities (see European Patent Application No. 146279 A, last page). Additional references include U.S. Pat. No. 4,618,365 (EP 146279-A), U.S. Pat. Nos. 4,826,529, 4,830, 661, 4,956,469, 5,003,075, 5,019,152, 5,120,346, 5,342,954, 5,344,814, 5,347,009, 5,347,010 and 5,362,704.

There have been found novel of the formula

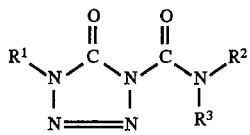

(I)

wherein

R$^1$ represents cycloalkenyl which may optionally be substituted by halogen or C$_{1-4}$ alkyl, or bicycloalkenyl which may optionally be substituted by halogen or C$_{1-4}$ alkyl, and R$^2$ and R$^3$ each independently represents alkyl, cycloalkyl, phenyl, substituted phenyl (said substituent being selected from nitro, cyano, halogen, alkyl, haloalkyl, alkoxy, haloalkoxy and alkylthio), alkenyl or alkynyl, or R$^2$ and R$^3$ may optionally form, together with the N-atom to which they are bonded, a 5- or 6-membered heterocyclic ring which may optionally contain a further hetero atom, and said heterocyclic ring may optionally be benzo-condensed and/or be substituted by C$_{1-4}$ alkyl.

The novel compounds of the formula (I), according to the invention, can be obtained by a process in which
(a): compounds of the formula:

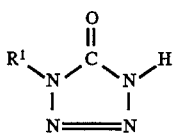

(II)

wherein

R$^1$ has the same definition as above,
are reacted with compounds of the formula:

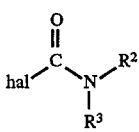

(III)

wherein

R$^2$ and R$^3$ have the same definitions as above and hal represents a leaving group such as a chlorine atom or bromine atom, in the presence of inert solvents and, if appropriate, in the presence of acid binders.

The compounds of formula (I) according to the invention have strong herbicidal activities.

Surprisingly, the tetrazolinone derivatives of the above formula (I) provided by the invention, substantially exhibit extremely superior herbicidal activities as compared with compounds specifically disclosed in the specification of the European Patent Application No. 0146279-A.

In the present specification, "cycloalkenyl" represents, for example, 1-cyclopenten-1-yl, 2-cyclopenten-1-yl, 3-cyclopenten -1-yl, 1-cyclohexen-1-yl, 2-cyclohexen-1-yl, 3-cyclohexen -1-yl, and the like, and such cycloalkenyl may optionally be substituted by a substituent selected from methyl, fluorine, chlorine, bromine, and the like.

"Bicycloalkenyl" represents, for example, bicyclo[2,2,1]hept-2-en-2-yl, bicyclo[2,2,1]hept-5-en-2-yl and the like, and such bicycloalkenyl may optionally be substituted by a substituent selected from methyl, fluorine, chlorine, bromine, and the like.

"Alkyl" represents alkyl groups in straight chain or branched chain and, as examples, there may be mentioned methyl, ethyl, propyl, isopropyl, n-, iso-, sec- or tert-butyl, n-, iso-, sec-, tert- or neo-pentyl, n-, iso-, sec-, tert- or neo-hexyl, and the like.

"Cycloalkyl" represents alkyl groups in a cyclic ring and, as examples, there may be mentioned cyclopropyl, cyclobutyl, cyclopentyl, cyclohexyl , cycloheptyl, cyclooctyl, and the like.

"Alkenyl" represents alkenyl groups in straight chain or blanched chain and, as examples, there may be mentioned vinyl, allyl, isopropenyl, 1-methyl-2-propenyl, 1,1-dimethyl-2-propenyl, 2- or 3-butenyl, 2-, 3- or 4-pentenyl and the like.

"Halogen" represents fluorine, chlorine, bromine or iodine, preferably being fluorine, chlorine or bromine.

"Alkynyl" represents alkynyl groups in straight chain or branched chain and, for example, there may be mentioned propargyl.

"5- or 6-membered heterocyclic ring" represents 5- or 6-membered heterocyclic rind which contain at least one nitrogen atom and may optionally contain a further heteroatom selected from a nitrogen atom, oxygen atom and sulfur atom, and such heterocyclic rings may further optionally be benzo-condensed.

Examples of such heterocyclic rings include the following radicals: pyrrolidinyl, pyrrolinyl, imidazolidinyl, pyrazolidinyl, pyrazolinyl, piperidinyl, piperazinyl, indolinyl, morpholinyl, 1,2,3,4-tetrahydroquinolinyls and the like, and such heterocyclic radicals may optionally be substituted by C$_{1-4}$ alkyl.

Among the compounds of formula (I) according to the invention, preferred compounds are those wherein R$^1$ represents C$_{3-8}$ cycloalkenyl which may optionally be substituted by halogen or C$_{1-4}$ alkyl, or C$_{6-8}$ bicycloalkenyl which may optionally be substituted by halogen or C$_{1-4}$ alkyl, and R$^2$ and R$^3$ each independently represents C$_{1-8}$ alkyl, C$_{3-8}$ cycloalkyl, phenyl, or substituted phenyl (said substituent being selected from nitro, cyano, halogen, C$_{1-4}$ alkyl, C$_{1-4}$ haloalkyl, C$_{1-4}$ alkoxy, C$_{1-4}$ haloalkoxy and C$_{1-4}$ alkylthio), C$_{2-8}$ alkenyl or C$_{3-8}$ alkynyl, or R$^2$ and R$^3$ may optionally form, together With the N-atom to which they are bonded, a 5- or 6-membered heterocyclic ring which may optionally contain a further hetero atom selected from a nitrogen atom, oxygen atom and sulfur atom, said heterocyclic ring being optionally, benzo-condensed and/or substituted by C$_{1-3}$ alkyl.

Among the compounds of formula (I) according to the invention, more preferred compounds are those wherein R$^1$ represents C$_{5-8}$ cycloalkenyl which may optionally be substituted by fluorine, chlorine, bromine or methyl, or $C_{6-8}$ bicycloalkenyl which may optionally be substituted by fluorine, chlorine, bromine or methyl, and $R^2$ and $R^3$ each independently represent $C_{1-6}$ alkyl, cyclopropyl, cyclopentyl, cyclohexyl, substituted phenyl (said substituent being selected from nitro, cyano, fluorine, chlorine, bromine, methyl, ethyl, trifluoromethyl, methoxy, ethoxy, trifluoromethoxy, methylthio and trifluoromethylthio), $C_{2-6}$ alkenyl or $C_{3-6}$ alkynyl, or $R^2$ and $R^3$ may optionally form, together with the N-atom to which they are bonded, pyrrolidin-1-yl, 2-methylpyrrolidin-1-yl, piperidino, 2-methylpiperidino, piperazin-1-yl, morpholino, 1,2,3,4-tetrahydroquinolin-1-yl, 2-methyl-1,2,3,4-tetrahydroquinolin-1-yl, 2,2-dimethyl-1,2,3,4-tetrahydroquinolin-1-yl, indolin-1-yl, 2-methylindolin-1-yl, or 2,2-dimethylindolin-1-yl.

Compounds of formula (I), according to the invention, are mentioned in the following Table 1 and Table 2 in addition to the compounds shown in the application examples hereinafter. Tables 1-1 to 1-8 illustrate those in which $R^2$ and $R^3$ represent groups which are independent of each other and Table 2 illustrates those in which $R^2$ and $R^3$ represent heterocyclic ring together with the N-atom to which they are bonded.

TABLE 1-1

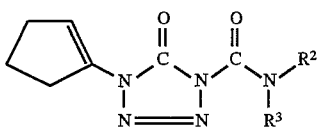

| $R^2$ | $R^3$ |
|---|---|
| ethyl | ethyl |
| ethyl | cyclohexyl |
| isopropyl | cyclohexyl |
| n-propyl | cyclopropyl |
| allyl | allyl |
| propargyl | propargyl |
| isopropyl | phenyl |
| isopropyl | 2-fluorophenyl |
| isopropyl | 4-fluorophenyl |
| isopropyl | 3-chlorophenyl |
| isopropyl | 4-chlorophenyl |
| isopropyl | 3,5-dichlorophenyl |
| isopropyl | 3-bromophenyl |
| isopropyl | 4-bromophenyl |
| isopropyl | 3-trifluoromethylphenyl |
| isopropyl | 4-methoxyphenyl |
| isopropyl | 3-trifluoromethoxylphenyl |
| isopropyl | 3-trifluoromethylthiophenyl |
| isopropyl | 3-methylphenyl |
| isopropyl | 4-methylphenyl |
| isopropyl | 4-nitrophenyl |
| isopropyl | 4-cyanophenyl |
| propargyl | phenyl |
| 1-methyl-2-propynyl | phenyl |
| 1,1-dimethyl-2-propynyl | phenyl |
| allyl | phenyl |
| methyl | phenyl |
| ethyl | phenyl |
| n-propyl | phenyl |
| n-butyl | phenyl |
| sec-butyl | phenyl |
| isobutyl | phenyl |
| 1-methyl-2-propynyl | 4-chlorophenyl |
| 1-methyl-2-propynyl | 4-bromophenyl |
| 1,1-dimethyl-2-propynyl | 4-chlorophenyl |
| 1,1-dimethyl-2-propynyl | 4-bromophenyl |
| 1,1-dimethyl-2-propynyl | 4-methylphenyl |

TABLE 1-1-continued

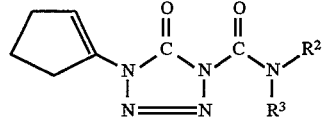

| $R^2$ | $R^3$ |
|---|---|
| 1,1-dimethyl-2-propynyl | 2-fluorophenyl |
| 1,1-dimethyl-2-propynyl | 3-fluorophenyl |
| 1,1-dimethyl-2-propynyl | 4-fluorophenyl |
| 1-methyl-2-propynyl | 2-fluorophenyl |
| 1-methyl-2-propynyl | 3-fluorophenyl |
| 1-methyl-2-propynyl | 4-fluorophenyl |
| isopropyl | benzyl |
| isopropyl | 4-chlorobenzyl |
| isopropyl | 4-fluorobenzyl |
| isopropyl | 3-trifluoromethylbenzyl |
| 1-methyl-2-propynyl | benzyl |
| 1,1-dimethyl-2-propynyl | benzyl |
| 1,1-dimethyl-2-propynyl | 4-chlorobenzyl |

TABLE 1-2

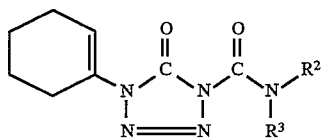

| $R^2$ | $R^3$ |
|---|---|
| ethyl | ethyl |
| ethyl | cyclohexyl |
| isopropyl | cyclohexyl |
| n-propyl | n-propyl |
| n-propyl | cyclopropyl |
| allyl | allyl |
| isopropyl | phenyl |
| isopropyl | 2-fluorophenyl |
| isopropyl | 3-fluorophenyl |
| isopropyl | 4-fluorophenyl |
| isopropyl | 2-chlorophenyl |
| isopropyl | 3-chlorophenyl |
| isopropyl | 4-chlorophenyl |
| isopropyl | 3-bromophenyl |
| isopropyl | 4-bromophenyl |
| isopropyl | 3-trifluoromethylphenyl |
| isopropyl | 4-methoxyphenyl |
| isopropyl | 2-trifluoromethoxyphenyl |
| isopropyl | 3-difluoromethoxyphenyl |
| isopropyl | 2-methylphenyl |
| isopropyl | 3-methylphenyl |
| isopropyl | 4-methylphenyl |
| isopropyl | 4-ethylphenyl |
| isopropyl | 4-cyanophenyl |
| isopropyl | 4-methylcarbonylphenyl |
| propargyl | phenyl |
| 1-methyl-2-propynyl | phenyl |
| 1,1-dimethyl-2-propynyl | phenyl |
| allyl | phenyl |
| methyl | phenyl |
| ethyl | phenyl |
| n-propyl | phenyl |
| n-butyl | phenyl |
| sec-butyl | phenyl |
| isobutyl | phenyl |
| 1-methyl-2-propynyl | 4-chlorophenyl |
| 1-methyl-2-propynyl | 4-bromophenyl |
| 1-methyl-2-propynyl | 4-methylphenyl |
| 1,1-dimethyl-2-propynyl | 4-chlorophenyl |
| 1,1-dimethyl-2-propynyl | 4-bromophenyl |
| 1,1-dimethyl-2-propynyl | 3-methylphenyl |
| 1,1-dimethyl-2-propynyl | 4-methoxyphenyl |

TABLE 1-2-continued

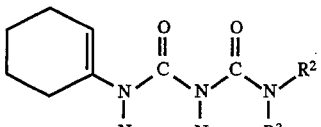

| R² | R³ |
|---|---|
| 1,1-dimethyl-2-propynyl | 2-fluorophenyl |
| 1,1-dimethyl-2-propynyl | 3-fluorophenyl |
| 1,1-dimethyl-2-propynyl | 4-fluorophenyl |
| 1-methyl-2-propynyl | 4-fluorophenyl |
| isopropyl | benzyl |
| isopropyl | 4-chlorobenzy |
| isopropyl | 4-fluorobenzyl |
| isopropyl | 2-fluorobenzyl |
| isopropyl | 4-cyanobenzyl |
| 1,1-dimethyl-2-propynyl | 4-cyanobenzyl |

TABLE 1-3

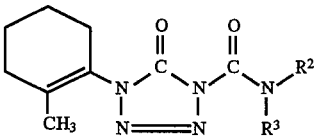

| R² | R³ |
|---|---|
| ethyl | ethyl |
| ethyl | cyclohexyl |
| isopropyl | cyclohexyl |
| n-propyl | n-propyl |
| n-propyl | cyclopropyl |
| n-propyl | cyclopentyl |
| isopropyl | phenyl |
| isopropyl | 2-fluorophenyl |
| isopropyl | 3-fluorophenyl |
| isopropyl | 4-fluorophenyl |
| isopropyl | 4-chlorophenyl |
| isopropyl | 2-chloro-4-methylphenyl |
| isopropyl | 4-bromophenyl |
| isopropyl | 3-methylphenyl |
| isopropyl | 4-methylphenyl |
| isopropyl | 4-cyanophenyl |
| propargyl | phenyl |
| 1-methyl-2-propynyl | phenyl |
| 1,1-dimethyl-2-propynyl | phenyl |
| allyl | phenyl |
| ethyl | phenyl |
| n-propyl | phenyl |
| n-butyl | phenyl |
| sec-butyl | phenyl |
| isobutyl | phenyl |
| 1-methyl-2-propynyl | 2-chlorophenyl |
| 1-methyl-2-propynyl | 4-chlorophenyl |
| 1-methyl-2-propynyl | 2-bromophenyl |
| 1-methyl-2-propynyl | 4-bromophenyl |
| 1-methyl-2-propynyl | 4-methylphenyl |
| 1,1-dimethyl-2-propynyl | 3-chlorophenyl |
| 1,1-dimethyl-2-propynyl | 4-chlorophenyl |
| 1,1-dimethyl-2-propynyl | 4-bromophenyl |
| 1,1-dimethyl-2-propyhyl | 4-fluorophenyl |
| 1,1-dimethyl-2-propynyl | 2,4-dichlorophenyl |
| 1-methyl-2-propynyl | 2-fluorophenyl |
| 1-methyl-2-propynyl | 4-fluorophenyl |
| isopropyl | benzyl |
| isopropyl | 4-fluorobenzyl |
| isopropyl | 3-trifluoromethylbenzyl |

TABLE 1-4

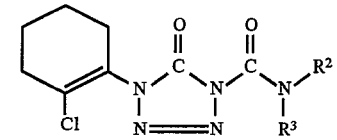

| R² | R³ |
|---|---|
| ethyl | ethyl |
| ethyl | cyclohexyl |
| isopropyl | cyclohexyl |
| n-propyl | cyclopropyl |
| n-propyl | cyclopentyl |
| allyl | allyl |
| isopropyl | phenyl |
| isopropyl | 2-fluorophenyl |
| isopropyl | 3-fluorophenyl |
| isopropyl | 4-fluorophenyl |
| isopropyl | 2-chlorophenyl |
| isopropyl | 4-chlorophenyl |
| isopropyl | 2,4-dichlorophenyl |
| isopropyl | 2-bromophenyl |
| isopropyl | 4-bromophenyl |
| isopropyl | 2-difluoromethoxyphenyl |
| isopropyl | 4-methylphenyl |
| propargyl | phenyl |
| 1-methyl-2-propynyl | phenyl |
| 1,1-dimethyl-2-propynyl | phenyl |
| allyl | phenyl |
| ethyl | phenyl |
| n-propyl | phenyl |
| n-butyl | phenyl |
| sec-butyl | phenyl |
| isobutyl | phenyl |
| 1-methyl-2-propynyl | 4-chlorophenyl |
| 1-methyl-2-propynyl | 4-bromophenyl |
| 1-methyl-2-propynyl | 4-methylphenyl |
| 1,1-dimethyl-2-propynyl | 2-chloropheny |
| 1,1-dimethyl-2-propynyl | 4-chlorophenyl |
| 1,1-dimethyl-2-propynyl | 4-fluorophenyl |
| 1-methyl-2-propynyl | 4-fluorophenyl |
| isopropyl | benzyl |
| isopropyl | 1-phenylethyl |
| isopropyl | 4-fluorophenyl |
| 1,1-dimethyl-2-propynyl | benzyl |

TABLE 1-5

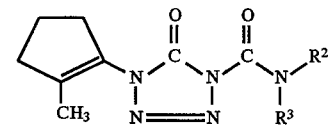

| R² | R³ |
|---|---|
| ethyl | ethyl |
| ethyl | cyclohexyl |
| isopropyl | cyclohexyl |
| n-propyl | cyclopropyl |
| propargyl | propargyl |
| isopropyl | phenyl |
| isopropyl | 4-fluorophenyl |
| isopropyl | 4-chlorophenyl |
| isopropyl | 4-bromophenyl |
| isopropyl | 3-methoxyphenyl |
| isopropyl | 4-methylphenyl |
| propargyl | phenyl |
| 1-methyl-2-propynyl | phenyl |
| 1,1-dimethyl-2-propynyl | phenyl |
| allyl | phenyl |
| n-propyl | phenyl |
| n-butyl | phenyl |
| sec-butyl | phenyl |

TABLE 1-5-continued

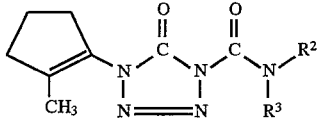

| R² | R³ |
|---|---|
| isobutyl | phenyl |
| 1-methyl-2-propynyl | 3,5-dichlorophenyl |
| 1,1-dimethyl-2-propynyl | 4-chlorophenyl |
| 1,1-dimethyl-2-propynyl | 4-bromophenyl |
| 1,1-dimethyl-2-propynyl | 4-fluorophenyl |
| isopropyl | benzyl |

TABLE 1-6

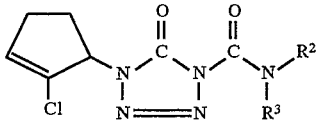

| R² | R³ |
|---|---|
| ethyl | ethyl |
| ethyl | cyclohexyl |
| isopropyl | cyclohexyl |
| isopropyl | cyclopropyl |
| isopropyl | cyclopentyl |
| methyl | isopropyl |
| isopropyl | phenyl |
| isopropyl | 4-fluorophenyl |
| isopropyl | 3-fluorophenyl |
| isopropyl | 4-chlorophenyl |
| isopropyl | 4-cyanophenyl |
| isopropyl | 4-methylphenyl |
| ethyl | phenyl |
| sec-butyl | phenyl |
| isobutyl | phenyl |
| n-propyl | phenyl |
| 1,1-dimethyl-2-propynyl | phenyl |
| 1-methyl-2-propynyl | phenyl |

TABLE 1-7

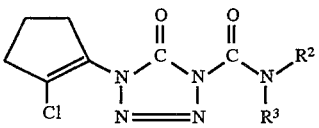

| R² | R³ |
|---|---|
| ethyl | ethyl |
| ethyl | cyclohexyl |
| isopropyl | cyclohexyl |
| n-propyl | cyclopropyl |
| n-propyl | cyclopentyl |
| isopropyl | phenyl |
| isopropyl | 4-chlorophenyl |
| isopropyl | 4-fluorophenyl |
| isopropyl | 2-fluorophenyl |
| isopropyl | 3-bromophenyl |
| isopropyl | 4-trifluoromethylphenyl |
| isopropyl | 4-trifluoromethoxyphenyl |
| isopropyl | 4-methylphenyl |
| isopropyl | 4-cyanophenyl |
| 1-methyl-2-propynyl | phenyl |
| 1,1-dimethyl-2-propynyl | phenyl |
| n-propyl | phenyl |
| n-butyl | phenyl |

TABLE 1-7-continued

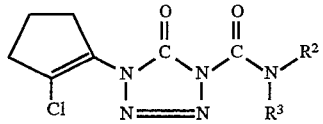

| R² | R³ |
|---|---|
| sec-butyl | phenyl |
| 1-methyl-2-propynyl | 4-chlorophenyl |
| 1,1-dimethyl-2-propynyl | 4-chlorophenyl |
| 1,1-dimethyl-2-propynyl | 4-fluorophenyl |
| isopropyl | benzyl |

TABLE 1-8

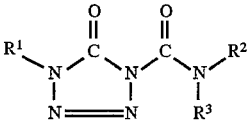

| R¹ | R² | R³ |
|---|---|---|
| 2-cyclohexen-1-yl | isopropyl | phenyl |
| 3-cyclohexen-1-yl | isopropyl | phenyl |
| 3-methyl-1-cyclohexen-1-yl | isopropyl | phenyl |
| 4-methyl-1-cyclohexen-1-yl | isopropyl | phenyl |
| 5-methyl-1-cyclohexen-1-yl | isopropyl | phenyl |
| 6-methyl-1-cyclohexen-1-yl | isopropyl | phenyl |
| 2-ethyl-1-cyclohexen-1-yl | isopropyl | phenyl |
| bicyclo[2,2,1]hept-5-en-2-yl | isopropyl | phenyl |
| bicyclo[2,2,1]hept-2-en-2-yl | isopropyl | phenyl |
| 2-chloro-2-cyclohexen-1-yl | ethyl | ethyl |
| 2-chloro-2-cyclohexen-1-yl | ethyl | cyclohexyl |
| 2-chloro-2-cyclohexen-1-yl | isopropyl | phenyl |
| 2-chloro-2-cyclohexen-1-yl | isopropyl | 4-fluorophenyl |
| 2-chloro-2-cyclohexen-1-yl | isopropyl | 4-methylphenyl |
| 2-chloro-2-cyclohexen-1-yl | 1-methyl-2-propynyl | phenyl |
| 2-chloro-2-cyclohexen-1-yl | 1,1-dimethyl-2-propynyl | phenyl |

TABLE 2

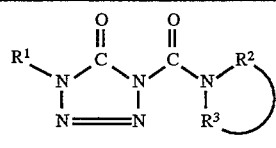

| R¹ | R²/R³ |
|---|---|
| cyclopenten-1-yl | pyrrolidin-1-yl |
| cyclopenten-1-yl | 1,2,3,4-tetrahydroquinolin-1-yl |
| cyclopenten-1-yl | 2-methyl-1,2,3,4-tetrahydroquinolin-1-yl |
| cyclopenten-1-yl | 2,2,-dimethyl-1,2,3,4-tetrahydroquinolin-1-yl |
| cyclopenten-1-yl | 2-methylindolin-1-yl |
| cyclopenten-1-yl | 2,2-dimethylindolin-1-yl |
| cyclohenxen-1-yl | pyrrolidin-1-y |
| cyclohenxen-1-yl | 2-methylpyrrolidin-1-yl |
| cyclohenxen-1-yl | indolin-1-yl |
| cyclohenxen-1-yl | 2-methylindolin-1-yl |
| cyclohenxen-1-yl | 2,2-dimethylindolin-1-yl |
| cyclohenxen-1-yl | 1,2,3,4-tetrahydroquinolin-1-yl |
| cyclohenxen-1-yl | 2-methyl-1,2,3,4-tetrahydroquinolin-1-yl |

TABLE 2-continued

| R¹ | R² / R³ |
|---|---|
| cyclohenxen-1-yl | 2,2-dimethyl-1,2,3,4-tetrahydroquinolin-1-yl |
| 2-methylcyclohenxen-1-yl | 2-methylindolin-1-yl |
| 2-methylcyclohenxen-1-yl | 2,2-dimethylindolin-1-yl |
| 2-methylcyclohenxen-1-yl | 2-methyl-1,2,3,4-tetrahydroquinolin-1-yl |
| 2-methylcyclohenxen-1-yl | 2,2-dimethyl-1,2,3,4-tetrahydroquinolin-1-yl |
| 2-chlorocyclohenxen-1-yl | 2-methylindolin-1-yl |
| 2-chlorocyclohenxen-1-yl | 2,2-dimethylindolin-1-yl |
| 2-chlorocyclohenxen-1-yl | 1,2,3,4-tetrahydroquinolin-1-yl |
| 2-chlorocyclohenxen-1-yl | 2-methyl-1,2,3,4-tetrahydroquiolin-1-yl |
| 2-chlorocyclohenxen-1-yl | 2,2-dimethyl-1,2,3,4-tetrahydroquinolin-1-yl |
| 2-methylcyclopenten-1-yl | 2-methyl-1,2,3,4-tetrahydroquinolin-1-yl |
| 2-methyl-2-cyclopenten-1-yl | 2-methyl-1,2,3,4-tetrahydroquinolin-1-yl |
| 2-chlorocyclopenten-1-yl | 2-methylpyrrolidin-1-yl |
| 2-chlorocyclopenten-1-yl | 2-methylindolin-1-yl |
| 2-chlorocyclopenten-1-yl | 2,2-dimethylindolin-1-yl |
| 2-chlorocyclopenten-1-yl | 2-methyl-1,2,3,4-tetrahydroquinolin-1-yl |
| 2-chlorocyclopenten-1-yl | 2,2-dimethyl-1,2,3,4-tetrahydroquinolin-1-yl |

When in the process (a), for example, 1-(cyclohexen-1-yl)-5(4H)-tetrazolinone and diethylcarbamoyl chloride are used as the starting materials, the course of the reaction can be represented by the following equation:

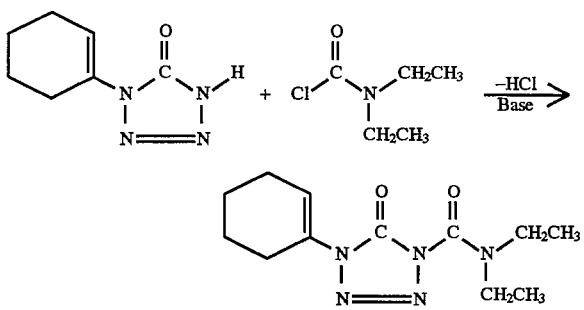

In the starting compounds of formula (II), employed in process (a), $R^1$ has the same meanings and preferred meanings as defined above for $R^1$ in formula (I).

The compounds of formula (II) are novel, and can be obtained by the following processes:
(b) compounds of the formula:

$$R^1\text{—NCO} \qquad (IV)$$

wherein
$R^1$ is defined as above,
are reacted with trimethylsilyl azide, if appropriate, in the presence of catalysts,
or (c) compounds represented by the above formula (IV) are reacted with sodium azide,
in the presence of inert solvents, and if appropriate in the presence of catalysts,
or
(d) compounds of the formula:

$$R^1-\overset{\overset{\displaystyle O}{\|}}{C}-Cl \qquad (V)$$

wherein
$R^1$ is defined as above,
are reacted with trimethylsilyl azide, and then are reacted with protic solvents.

In the above production method (b) and production method (c), the compounds of formula (IV), used as the starting materials, are well known in the field of organic chemistry and, for example, there may be mentioned:
1-cyclopenten-1-yl isocyanate,
2-methyl-1-cyclopenten-1-yl isocyanate,
2-cyclopenten-1-yl isocyanate,
2-chloro-2-cyclopenten-1-yl isocyanate,
1-cyclohexen-1-yl isocyanate,
2-methyl-1-cyclohexen-1-yl isocyanate,
2-chloro-1-cyclohexen-1-yl isocyanate,
2-cyclohexen-1-yl isocyanate and,
3-cyclohexen-1-yl isocyanate.

The compounds of formula (IV) can also be easily produced by applying Curtius rearrangement reaction to the compounds represented by the above formula (V). This reaction can be conducted by a synthetic method analogous to that described in The Journal of Organic Chemistry, 1989, Vol. 52, page 224, id. 1961, Vol. 26, page 3511; Synthesis, 1972, page 551; or Journal of American Chemical society, 1972, Vol. 94, page 6203.

The reaction in the production method (b) can be conducted by a method analogous to that described in J. Org. Chem. Vol.45, 1980, pages 5130–5136.

Preparation method (c) can be conducted similarly to the method described in J. Am. Chem. Soc. Vol. 81, 1959, pages 3076–3079 or the specification of Japanese Application Hei 6-130873.

In the above method (d), the compounds of formula (V), used as the starting materials, are well known in the field of organic chemistry and, for example, there may be mentioned.
2-chloro-1-cyclohexenecarbonyl chloride,
2-methyl-1-cyclohexenecarbonyl chloride,
2-chloro-2-cyclohexenecarbonyl chloride,
2-methyl-2-cyclohexenecarbonyl chloride,
3-chloro-1-cyclohexenecarbonyl chloride,
6-methyl-1-cyclohexenecarbonyl chloride,
1-cyclohexenecarbonyl chloride,
2-chloro-1-cyclopentenecarbonyl chloride and,
1-cyclopentenecarbonyl chloride.

The compounds of the formula (V) can also be easily obtained by chlorinating compounds of the formula:

$$R^1-\overset{\overset{\displaystyle O}{\|}}{C}-OH \qquad (VI)$$

wherein
$R^1$ is as defined above,
according to any conventional method.

The compounds of formula (VI) are well known in the field of organic chemistry and examples thereof include the following compounds:

2-chloro-1-cyclohexenecarboxylic acid,
2-methyl-1-cyclohexenecarboxylic acid,
2-chloro-2-cyclohexenecarboxylic acid,
2-methyl-2-cyclohexenecarboxylic acid
3-chloro-1-cyclohexenecarboxylic acid,
6-methyl-1-cyclohexenecarboxylic acid,
1-cyclohexenecarboxylic acid,
2-chloro-1-cyclopentenecarboxylic acid and,
1-cyclopentenecarboxylic acid.

Preparation method (d) can be conducted by a method analogous to that described in J. Chem. Soc., Perkin Trans. 1, 1992, pages 1101–1104 or J. Am. Chem. Soc., Vol. 81, 1959, pages 3076–3079.

In preparation method (a), examples of the compounds of formula (II) used as starting materials include the following compounds:
1-(cyclohexen-1-yl)-5(4H)-tetrazolinone,
1-(2-chlorocyclohexen-1-yl)-5(4H)-tetrazolinone,
1-(2-methylcyclohexen-1-yl)-5(4H)-tetrazolinone,
1-(2-cyclohexen-1-yl)-5(4H)-tetrazolinone,
1-(2-chloro-2-cyclohexen-1-yl)-5(4H)-tetrazolinone,
1-(2-methyl-2-cyclohexen-1-yl)-5(4H)-tetrazolinone,
1-(3-cyclohexen-1-yl)-5(4H)-tetrazolinone,
1-(6-cyclohexen-1-yl)-5 (4H)-tetrazolinone,
1-(cyclopenten-1-yl)-5 (4H)-tetrazolinone,
1-(2-chlorocyclopenten-1-yl)-5(4H)-tetrazolinone,
1-(2-methylcyclopenten-1-yl)-5 (4H )-tetrazolinone,
1-(2-cyclopenten-1-yl)-5 (4H)-tetrazolinone,
1-(2-chloro-2-cyclopenten-1-yl)-5 (4H)-tetrazolinone and,
1-(2-methyl-2-cyclopenten-1-yl)-5 (4H)-tetrazolinone.

In preparation method (a), the compounds of formula (III) also used as starting materials are well known in the field of organic chemistry (commercially available as a reagent) and examples thereof include the following compounds:
diisopropylcarbamoyl chloride (and bromide),
diethylcarbamoyl chloride (and bromide),
dimethylcarbamoyl chloride (and bromide),
N-methyl-N-ethylcarbamoyl chloride (and bromide),
N-methyl-N-n-propylcarbamoyl chloride (and bromide),
N-methyl-N-isopropylcarbamoyl chloride (and bromide),
N-methyl-N-cyclopropylcarbamoyl chloride (and bromide),
N-methyl-N-s-butylcarbamoyl chloride (and bromide),
N-methyl-N-cyclopentylcarbamoyl chloride (and bromide),
N-methyl-N-cyclohexylcarbamoyl chloride (and bromide),
N-methyl-N-phenylcarbamoyl chloride (and bromide),
N-methyl-N-(1-methyl-2-propenyl)carbamoyl chloride (and bromide),
N-ethyl-N-n-propylcarbamoyl chloride (and bromide),
N-ethyl-N-isopropylcarbamoyl chloride (and bromide),
N-ethyl-N-cyclopropylcarbamoyl chloride (and bromide),
N-ethyl-N-s-butylcarbamoyl chloride (and bromide),
N-ethyl-N-cyclopentylcarbamoyl chloride (and bromide),
N-ethyl-N-cyclohexylcarbamoyl chloride (and bromide),
N-ethyl-N-phenylcarbamoyl chloride (and bromide),
N-n-propyl-N-isopropylcarbamoyl chloride (and bromide),
N-n-propyl-N-cyclopropylcarbamoyl chloride (and bromide),
N-n-propyl-N-s-butylcarbamoyl chloride (and bromide),
N-n-propyl-N-cyclopentylcarbamoyl chloride (and bromide),
N-n-propyl-N-cyclohexylcarbamoyl chloride (and bromide),
N-isopropyl-N-phenylcarbamoyl chloride (and bromide),
N-isopropyl-N-allylcarbamoyl chloride (and bromide),
pyrrolin-1-ylcarbonyl chloride (and bromide),
piperidinocarbonyl chloride (and bromide),
morpholinocarbonyl chloride (and bromide),
2-methylpiperidinocarbonyl chloride (and bromide),
2,5-dimethylpyrrolidin-1-ylcarbonyl chloride (and bromide),
2,6-dimethylpiperidinocarbonyl chloride (and bromide),
indolin-1-ylcarbonyl chloride (and bromide),
2-methylindolin-1-ylcarbonyl chloride (and bromide),
2,2-dimethylindolin-1-ylcarbonyl chloride (and bromide),
1,2,3,4-tetrahydroquinolin-1-ylcarbonyl chloride (and bromide),
2-methyl-1,2,3,4-tetrahydroquinolin-1-ylcarbonyl chloride (and bromide) and,
2,2-dimethyl-1,2,3,4-tetrahydroquinolin-1-ylcarbonyl chloride (and bromide).

The reaction in preparation method (a) may usually be carried out in a diluent and useful appropriate diluents include any inert organic solvents. Examples of such diluents include aliphatic, alicyclic and aromatic hydrocarbons (which may optionally be chlorinated) such as pentane, hexane, cyclohexane, petroleum ether, ligroin, benzene, toluene, xylene, dichloromethane, chloroform, carbon tetrachloride, 1,2-dichloroethane, chlorobenzene and dichlorobenzene; ethers such as diethyl ether, methyl ethyl ether, di-isopropyl ether, dibutyl ether, dioxane, dimethoxyethane (DME), tetrahydrofuran (THF) and diethyleneglycol dimethyl ether (DGM); nitriles such as acetonitirile and propionitrile; acid amides such as dimethylformamide (DMF), dimethylacetamide (DMA), N-methylpyrrolidone, 1,3-dimethyl-2-imidazolidinone and hexamethylphosphoric triamide (HMPA); sulfones and sulfoxides such as dimethylsulfoxide (DMSO) and sulfolane; bases such as pyridine; and the like.

Preparation method (a) can be carried out in the presence of an acid binding agent and useful acid binding agents are exemplified by inorganic bases such as hydroxides, carbonates, bicarbonates and alcoholatos of alkali metals including sodium hydrogen carbonate, potassium hydrogen carbonate, sodium carbonate, potassium carbonate, lithium hydroxide, sodium hydroxide, potassium hydroxide, potassium tert-butoxide, and the like; inorganic alkali metal amides including lithium amide, sodium amide, potassium amide and the like; and organic bases such as tertiary amines, dialkylaminoanilines and pyridines including triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO), 1,8-diazabicyclo[5,4,0]undec-7-ene (DBU), and the like.

Preparation method (a) can be conducted at temperatures within a broad range but it is preferable to carry it out generally in the temperature range of about −30° to about 200° C., preferably about −20° to about 130° C. Also, the reaction can be carried out under atmospheric pressure but may also be optionally operated under an elevated or reduced pressure.

Preparation method (a) can be carried out by reacting, for instance, 1 to 1.5 mols of the compound of formula (III) with 1 mol of the compound of formula (II), in a diluent such as toluene, in the presence of 1 to 1.5 mols of an acid binding agent, thereby to obtain the compound of formula (I).

The compounds of formula (I) according to the invention have, as shown in the test examples hereinbelow, excellent herbicidal activity so that they can be used as herbicides for controlling weeds.

The term "weeds" means all plants which grow in undesired loci.

The compounds according to the invention act as nonselective or selective herbicides in dependence on the concentration used.

The active compounds according to the invention can be used, for example, as selective herbicides in connection with the following weeds and cultivated plants:

Dicotyledon weeds of the genera: Sinapis, Lepidium, Galium, Stellaria, Chenopodium, Urtica, Senecio, Amaranthus, Portulaca, Xanthium, Ipomoea, Polygonum, Ambrosia, Cirsium, Sonchus, Solanum, Rorippa, Lamium, Veronica, Datura, Viola, Galeopsis, Papaver, Centaurea, Galinsoga, Rotala, Lindernia, etc.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita, etc.

Monocotyledon weeds of the genera: Echinochloa, Setaria, Panicum, Digitaria, Phleum, Poa, Festuca, Eleusine, Lolium, Bromus, Avena, Cyperus, Sorghum, Agropyron, Monochoria, Fimbristylis, Sagittaria, Eleocharis, Scirpus, Paspalum, Ischaemum, Agrostis, Alopecurus, Cynodon, etc.

Monocotyledon cultures of the genera: Oryza, Zea, Triticum, Hordeum, Avena, Secale, Sorghum, Panicum, Saccharum, Ananas, Asparagus, Allium, etc.

However, the use of the compounds according to the invention is in no way restricted to the above genera, but also extends in the same manner to other plants. Further, the compounds of the invention are suitable, depending on the concentration, for the total combating of weeds, for example on industrial terrain, rail tracks, and on paths and squares with or without tree plantings.

Equally, the inventive compounds can be employed for combating weeds in perennial cultures, for example aforestations, decorative tree plantations, orchards, vineyards, citrus groves, nuts orchards, banana plantations, coffee plantations, tea plantations, rubber plantations, oil palm plantations, cocoa plantations, soft fruit plantations and hopfields, and for the selective combating of weeds in annual cultures.

The active compounds of the invention can be converted into any form of conventional formulations in the uses thereof. Such formulation forms can be exemplified by solutions, wettable powders, emulsions, suspensions, powders, foams, pastes, granules, tablets, natural or synthetic materials impregnated with active compound, microcapsules, seed-coatings, ULV [cold mist and warm mist] and others.

These formulations can be prepared by any of the methods known per se and they can be produced by, for instance, mixing the active compound with a developing agent or, that is, a liquid diluent, solid diluent or, in some cases, a surface-active agent, namely, emulsifier and/or dispersant and/or foam-forming agent. In the case of using water as the developing agent, for example, an organic solvent can be used as the auxiliary solvent, if necessary.

Liquid diluents or liquid carriers are exemplified by aromatic hydrocarbons (e.g., xylene, toluene, alkylnaphthalene, etc.), chlorinated aromatic or chlorinated aliphatic hydrocarbons (e.g., chlorobenzenes, chlorinated ethylenes, chlorinated methylene, etc.), aliphatic hydrocarbons [e.g., cyclohexane, paraffins (such as petroleum fractions), etc.], alcohols (e.g., butanol, glycols, and ethers and esters thereof, etc.), ketones (e.g., acetone, methyl ethyl ketone, methyl isobutyl ketone, cyclohexanone, etc.), highly polar solvents (e.g., dimethyl formamide, dimethyl sulphoxide, etc.), and the like.

The solid extenders are exemplified by natural soil minerals (such as kaolin, clay, talc, chalk, quarts, attapulgite, montmorillonite, diatomaceous earth, etc.) and synthetic soil minerals (such as high-disperse silicic acid, alumina, silicate salts, etc.).

The solid carriers for granules are exemplified by ground and classified rocks (such as calcite, marble, pumice, sepiolite, dolomite, etc.), synthetic granules of inorganic or organic meals and granules of organic materials such as sawdust, coconut shells, corn and tobacco stalks.

As emulsifying agents and/or foam-forming agents there are suitable: for example non-ionic and anionic emulsifiers, such as polyoxyethylene-fatty acid esters and polyoxyethylene fatty alcohol ethers (for example alkylaryl polyglycol ethers, alkyl sulfonates, alkyl sulfates, aryl sulfonates) as well as albumin hydrolysis products.

As dispersing agents there are suitable: for example lignin sulphite waste liquors and methylcellulose.

Adhesives may also be used optionally in formulations (such as powders, granules and emulsifiers) and such adhesives are exemplified by carboxymethyl cellulose, natural and synthetic polymers (e.g., gum arabic, polyvinyl alcohol, polyvinyl acetate, etc.).

It is also possible to use colorants such as inorganic pigments; for example iron oxide, titanium oxide, and Prussian Blue, and organic dyestuffs, such as alizarin dyestuffs, azo dyestuffs and metal phthalocyanine dyestuffs, and trace nutrients such as salts of metals, for example iron, magnesium, boron, copper, molybdenum and zinc.

The formulations in general contain between 0.1 and 95 percent by weight, preferably between 0.5 and 90% by weight of the active compound of the invention.

The active compounds of the invention can be used, for controlling weeds, per se or in the form of formulations and can be mixed with any known herbicides. The mixture may be either prepared in advance in the form of a final formulation or prepared by tank-mixing immediately before use.

The known herbicides which can be used in combinations with the compound of the invention in the mixed formulations are exemplified by the followings:

for weed control in cereal cultivation,
4-amino-6-(1,1-dimethylethyl)-3-ethylthio-1,2,4-triazin-5(4H)-one, 1-amino-6-ethylthio-3-(2,2-dimethylpropyl)-1,3,5-triazin-2,4(1H,3H)-dione, N-(2-benzothiazolyl)-N,N'-dimethylurea, etc.

for weed control in cultivation of *Saccharum officinarum:*
4-amino-3-methyl-6-phenyl-1,2,4-triazin-5(4H)-one, etc.

for weed control in cultivation of Glycine:
4-amino-6-(1,1-dimethylethyl)-3-methylthio-1,2,4-triazin-5(4H)-one, etc.

Surprisingly, some of the compounds of the invention exhibit a synergistic effect when they are used in combination with other known herbicides.

The active compounds of the invention can be used per se or in the form of a formulation such as a liquid preparation for spreading, emulsion, suspension, powder, paste or granules, or in a use form prepared by further dilution.

The active compounds can be used by liquid watering, spraying, atomizing, granule scattering, etc.

The application period of the active compounds of the invention is not particularly restricted so that they can be applied at any stage of pre-emergence and post-emergence.

Furthermore, they can be incorporated into the soil before sowing.

The application concentration of the active compounds of the invention can be varied within a wide range depending on the nature of the desired effect, but, in use as a herbicide, the application concentration is exemplified by the range of about 0.001 kg/ha–about 10 kg/ha of the active compound, preferably 0.01 kg/ha–about 5 kg/ha.

Preparation and use of the compounds of the invention are shown in the following illustrative examples:

Synthesis Example 1

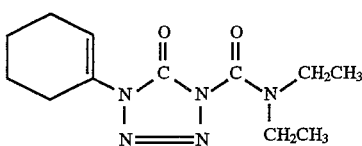
(Compound No. 1)

1-(Cyclohexen-1-yl)-5(4H)-tetrazolinone (1.5 g), diethylcarbamoyl chloride (1.5 g) and 4-dimethylaminopyridine (1.5 g) were suspended in toluene (50 ml) and agitated at 50°–55° C. for 6 hours. After cooling, the toluene layer was washed successively with 10% solution of hydrochloric acid, water, a saturated aqueous solution of sodium hydrogen carbonate and water and dried over anhydrous sodium sulfate. Then, toluene was distilled off under reduced pressure, and the residual oil was subjected to silica gel. Chromatography (chloroform) to yield 1-(chyclohenxen-1-yl)-4-(N,N-diethyl-carbamoyl)-5-(4H)-tetrazolinone (1.7 g). $n_D^{20}=1.5257$ Further compounds which are obtained by similar methods in Table 3:

TABLE 3

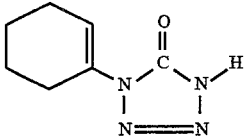

| Compound No. | $R^1$ | $R^2$ | $R^3$ | m.p. or refractive index |
|---|---|---|---|---|
| 2 | cyclohexen-1-yl | ethyl | cyclohexyl | $n_D^{20} = 1.5291$ |
| 3 | 2-chlorocyclo-hexen-1-yl | ethyl | ethyl | $n_D^{20} = 1.5208$ |
| 4 | cyclohexen-1-yl | isopropyl | phenyl | 84–87° C. |
| 5 | cyclohexen-1-yl | ethyl | phenyl | $n_D^{20} = 1.5605$ |
| 6 | cyclohexen-1-yl | n-propyl | phenyl | $n_D^{20} = 1.5575$ |
| 7 | cyclohexen-1-yl | isopropyl | 4-chlorophenyl | 97.5–99° C. |
| 8 | cyclohexen-1-yl | methyl | phenyl | $n_D^{20} = 1.5672$ |
| 9 | cyclohexen-1-yl | 1,2,3,4-tetrahydro-quinolin-1-yl | | $n_D^{20} = 1.5828$ |
| 10 | cyclopenten-1-yl | isopropyl | phenyl | 101.5–103° C. |
| 11 | cyclohexen-1-yl | isopropyl | 4-methylphenyl | 97–98.5° C. |
| 12 | 2-chlorocyclo-hexen-1-yl | isopropyl | phenyl | $n_D^{20} = 1.5400$ |
| 13 | 2-chlorocyclo-hexen-1-yl | ethyl | phenyl | 65–68.5° C. |
| 14 | 2-chlorocyclo-hexen-1-yl | ethyl | cyclohexyl | $n_D^{20} = 1.5229$ |
| 15 | cyclopenten-1-yl | ethyl | ethyl | $n_D^{20} = 1.5188$ |
| 16 | cyclopenten-1-yl | ethyl | cyclohexyl | $n_D^{20} = 1.5255$ |
| 17 | 2-chlorocyclo-penten-1-yl | isopropyl | phenyl | $n_D^{20} = 1.5500$ |
| 18 | 2-chloro-2-cyclopenten-1-yl | isopropyl | phenyl | $n_D^{20} = 1.5475$ |
| 19 | cyclopenten-1-yl | ethyl | phenyl | 66.5–68.5° C. |
| 20 | cyclopenten-1-yl | isopropyl | 4-chloro-phenyl | 144–145° C. |
| 21 | 2-chlorocyclo-penten-1-yl | isopropyl | 4-fluoro-phenyl | 76–77° C. |
| 22 | 2-chloro-2-cyclopenten-1-yl | isopropyl | 4-fluoro-phenyl | $n_D^{20} = 1.5260$ |
| 23 | cyclohexen-1-yl | isopropyl | 4-fluoro-phenyl | 88–90.5° C. |
| 24 | 2-chlorocyclo-hexen-1-yl | isopropyl | 4-fluoro-phenyl | 71–72° C. |
| 25 | 2-chlorocyclo-hexen-1-yl | isopropyl | 4-chloro-phenyl | 117–119° C. |
| 26 | cyclohexen-1-yl | 1-methyl-2-propynyl | phenyl | $n_D^{20} = 1.5400$ |

TABLE 3-continued

| Compound No. | $R^1$ | $R^2$ | $R^3$ | m.p. or refractive index |
|---|---|---|---|---|
| 27 | cyclohexen-1-yl | 1,1-di-methyl-2-propynyl | phenyl | $n_D^{20} = 1.5540$ |
| 28 | cyclohexen-1-yl | 2-methyl-1,2,3,4-tetra-hydroquinolin-1-yl | | $n_D^{20} = 1.5737$ |
| 29 | 6-methylcyclo-hexen-1-yl | isopropyl | phenyl | $n_D^{20} = 1.5410$ |
| 30 | cyclohexen-1-yl | sec-butyl | phenyl | $n_D^{20} = 1.5461$ |
| 31 | 2-chlorocyclo-hexen-1-yl | sec-butyl | phenyl | $n_D^{20} = 1.5278$ |

In the table, in compounds Nos. 9 and 28 $R^2$ and $R^3$ together with the nitrogen atom to which they are bonded form a heterocyclic ring.

SYNTHESIS OF STARTING MATERIALS

Synthesis Example 2

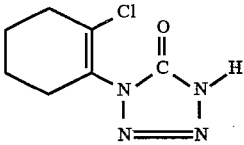

To a mixture of 1-cyclohexenyl isocyanate (11.0 g) and trimethylsilyl azide (15.4 g), a catalytic amount of boron trifluoride ethyl etherate was added to be heated with refluxing for 48 hours. After completing the reaction, the excess trimethylsilyl azide was distilled off under reduced pressure and methanol was added to the residue. Thereafter, the methanol was distilled off under reduced pressure and the residue was subjected to silica gel chromatography (chloroform:ethanol=15:1) to give 1-(cyclohexen-1-yl)-5(4H)-tetrazolinone (7.0 g). m.p. 119.5°–122° C.

In the same manner as in this Synthesis Example 2, 1-(cyclopenten-1-yl)-5(4H)-tetrazolinone was obtained. m.p. 137°–139° C.

Synthesis Example 3

To a mixture of 2-chloro-1-cyclohexenecarbonyl chloride (9.0 g) and trimethylsilyl azide (15 g), a catalytic amount of boron trifluoride ethyl etherate was added, and the mixture was heated with refluxing for 48 hours. After completing the reaction, the excess trimethylsilyl azide was distilled off under reduced pressure and methanol was added to the residue. Thereafter, methanol was distilled off under reduced pressure and the residue was subjected to silica gel chromatography (chloroform:ethanol=15:1) to give 1-(2-chlorocyclohexen-1-yl)-5(4H)-tetrazolinone (5.5 g). m.p. 130°–131° C.

In the same manner as in this Synthesis Example 3, 1-(cyclopenten-1-yl)-5(4H)-tetrazolinone, m.p. 137°–139° C., and 1(cyclohexen-1-yl)-5(4H)-tetrazolinone, m.p. 119.5°–122° C., were obtained.

BIOLOGICAL TEST EXAMPLES

Test Example 1

Herbicidal Effect Test Against Paddy Field Weeds

Preparation of formulations of active ingredients carrier: acetone, 5 parts by weight emulsifier: benzyloxypolyglycol ether, 1 part by weight The formulations of active ingredients are obtained as an emulsion by mixing 1 part by weight of the active compounds and the above amounts of carrier and emulsifier. The prescribed amount of the formulation is diluted with water to prepare a testing formulation.

Testing procedure

In the greenhouse, 3 seedlings of paddy rice (cultivar: Nipponbare) of 2.5 leafstage (15 cm tall) were transplanted in two places in 1/2000 are pot (25×25×9 cm) filled with paddy field soil. Then, seeds of barnyardgrass, cow hairs, small-flower, bulrush, monochoria, broad-leaved weeds (common falsepimpernel, Indian toothcup, long stemmed water wort, Ammannia multiflora Roxb. Dopatrium junceum Hamilt), water nutgrass, Japanese ribbon wapato were sowed, and water was poured on the soil to a depth of about 2–3 cm. To each a prescribed amount of the formulation was applied to the surface of the water 5 days after transplanting of the paddy rice.

The herbicidal effect was examined on the day after 3 weeks from the treatment during which period the water depth of 3 cm was maintained. The herbicidal effect was rated as 100% in the case of complete death and as 0% in the case where no herbicidal effect was observed.

Compounds Nos. 4, 7, 10, 11, 12, 17, 18, 21 and 23 of the invention (see Table 3) exhibited an adequate herbicidal effect (up to 100%) against paddy field weeds and exhibited safety (0% damage) against the transplanted paddy rice at application of 0.25 kg/ha of each active compound.

Test Example 2

Test of Pre-Emergence Soil Treatment Against Upland Weeds

Testing method

In the greenhouse, seeds of Echinochloa and *Amaranthus lividus* were sowed each in the surface layer of plowed land soil filled in a 120 cm² pot with soil-covering and over each a prescribed amount of the testing formulation prepared was uniformly spread on the surface layer of soil in the testing pot.

The herbicidal effect was examined after 4 weeks from sowing.

In this test, for example, Compounds Nos. 3, 9, 10, 17 and 22 of the invention (see Table 3) exhibited a herbicidal effect of 100% against Echinochloa and *Amaranthus lividus* by application of 1 kg/ha of active compound.

Test Example 3

Test of Post-emergence Foliage Treatment Against Upland Weeds

Testing method

In the greenhouse, seeds of Echinochloa and *Amaranthus lividus* were sowed each in a 120 cm³ pot filled with plowed land soil and covered with soil. After 10 days from sowing and soil-covering (when the weeds were in 2-foliage period on average), a prescribed amount of the formulation was uniformly spread on the foliage of the plant in the testing pot. After 3 weeks from spreading, the herbicidal effect was examined.

In this test, for example, Compounds Nos. 1, 3, 11, 21 and 22 of the invention (see Synthesis Example 1 and Table 3) exhibited a herbicidal effect of 100% against Echinochloa and *Amaranthus lividus* by application of 2 kg/ha of each active compound.

Formulation Example 1 (Granules)

Water (25 parts) is added to a mixture of Compound No. 3 (10 parts) of the invention, bentonite (montmorillonite) (30 parts), talc (58 parts) and lignin sulphonate salt (2 parts) with heading and formed in 10–40 mesh granules using an extrusion-type granulator followed by drying at 40°–50° C. to give granules.

Formulation Example 2 (Granules)

A clay mineral (95 parts) having a particle size distribution of 0.2–2 mm is introduced in a rotary mixer and compound No. 8 (5 parts) of the invention is sprayed therein with a liquid diluent under rotation uniformly to wet, followed by drying at 40°–500° C. giving granules.

Formulation Example 3 (Emulsion)

An emulsion is obtained by mixing Compound No. 20 (30 parts) of the invention, xylene (5 parts), polyoxyethylene alkyl phenyl ether (8 parts) and calcium alkylbenzene sulphonate (7 parts) with stirring.

Formulation Example 4 (Wettable Powder)

A wettable powder is prepared by mixing Compound No. 1 (15 parts) of the invention, a mixture (1:1) of White Carbon (fine powder of hydrated non-crystalline silicon oxide) (80 parts) and powdery clay, sodium alkylbenzene sulphonate (2 parts) and a condensate of sodium alkylnaphthalene sulphonate and formaldehyde (3 parts) in a powdery state.

Formulation Example 5 (Wettable Granules)

Wettable granules are prepared by thoroughly mixing. Compound No. 2 (20 parts) of the invention, sodium lignin sulphonate (30 parts), bentonite (15 parts) and calcined diatomaceous earth powder (35 parts) followed by addition of water and extrusion through a 0.3 mm screen and drying.

It will be understood that the specification and examples are illustrative but not limitative of the present invention and that other embodiments within the spirit and scope of the invention will suggest themselves to those skilled in the art.

We claim:
1. A compound of the formula

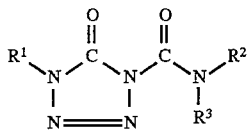

wherein
- $R^1$ is cycloalkenyl which may optionally be substituted by halogen or $C_{1-4}$ alkyl, or bicycloalkenyl which may optionally be substituted by halogen or $C_{1-4}$ alkyl, and
- $R^2$ and $R^3$ each independently is alkyl, cycloalkyl, phenyl (optionally substituted by a member selected from the group consisting of nitro, cyano, halogen, alkyl, haloalkyl, alkoxy, haloalkoxy and alkylthio), alkenyl and alkynyl, or $R^2$ and $R^3$ together with the N-atom to which they are bonded form an optionally $C_1$-$C_4$alkyl substituted 5- or 6- membered heterocyclic ring wherein said heterocyclic ring is selected from the group consisting of pyrrolidinyl, pyrrolinyl, imidazolidinyl, pyrazolidinyl, pyrazolinyl, piperidinyl, piperazinyl, indolinyl, morpholinyl, 1,2,3,4-tetrahydroquinolinyl.

2. A compound according to claim 1, wherein
$R^1$ is $C_{3-8}$ cycloalkenyl which may optionally be substituted by halogen or $C_{1-4}$ alkyl, or $C_{6-8}$ bicycloalkenyl which may optionally be substituted by halogen and $C_{1-4}$ alkyl, and $R^2$ and $R^3$ each independently is $C_{1-8}$ alkyl, $C_{3-8}$ cycloalkyl, phenyl, (optionally substituted by a member selected from the group consisting of nitro, cyano, halogen, $C_{1-4}$ alkyl, $C_{1-4}$ haloalkyl, $C_{1-4}$ alkoxy, $C_{1-4}$ haloalkoxy and $C_{1-4}$ alkylthio), $C_{2-8}$ alkenyl or $C_{3-8}$ alkynyl, $R^2$ and $R^3$ together with the N-atom to which they are bonded form an optionally $C_1$-$C_3$-alkyl substituted 5- or 6-membered heterocyclic ring wherein said heterocyclic ring is selected from the group consisting of pyrrolidinyl, pyrrolinyl, imidazolidinyl, pyrazolidinyl, pyrazolinyl, piperidinyl, piperazinyl, indolinyl, morpholinyl, 1,2,3,4-tetrahydroquinolinyl.

3. A compound according to claim 1, wherein
$R^1$ is $C_{5-8}$ cycloalkenyl which may optionally be substituted by fluorine, chlorine bromine or methyl, or $C_{6-8}$ bicycloalkenyl which may optionally be substituted by fluorine, chlorine, bromine and methyl, and $R^2$ and $R^3$ each independently is $C_{1-6}$ alkyl, cyclopropyl, cyclopentyl, cyclohexyl, phenyl (optionally substituted by a member selected from the group consisting of nitro, cyano, fluorine, chlorine, bromine, methyl, ethyl, trifluoromethyl, methoxy, ethoxy, trifluoromethoxy, methylthio and trifluoromethylthio), $C_{2-6}$ alkenyl and $C_{3-6}$ alkynyl, or $R^2$ and $R^3$ together with the N-atom to which they are bonded form a pyrrolidin-1-yl, 2-methyl-pyrrolidin-1-yl, piperidino, 2-methylpiperidino, piperazin-1-yl, morpholino, 1,2,3,4-tetrahydro-quinolin-1-yl, 2-methyl-1,2,3,4-tetrahydroquinolin-1-yl, 2,2-dimethyl-1,2,3,4-tetrahydro-quinolin-1-yl, indolin-1-yl, 2-methylindolin-1-yl, or 2,2-dimethylindolin-1-yl radical.

4. A compound according to claim 1, wherein such compound is 1-(2-chlorocyclohexen-1-yl)-4-(N,N-diethyl-carbamoyl)-5-(4H)-tetrazolinone.

5. A compound according to claim 1, wherein such compound is 1-(cyclohexen-1-yl) -4-(N-phenyl-N-isopropyl-carbamoyl)-5-(4H)-tetrazolinone.

6. A compound according to claim 1, wherein such compound is 1-(cyclohexen-1-yl) -4-[N-(4-methylphenyl)-N-isopropyl-carbamoyl]-5-(4H)-tetrazolinone.

7. A compound according to claim 1, wherein such compound is 1-(2-chlorocyclopenten-1-yl)-4-(N-phenyl-N-isopropyl-carbamoyl)-5-(4H)-tetrazolinone.

8. A compound according to claim 1, wherein such compound is 1-(2-chlorocyclopenten-1-yl)-4-[N-(4-fluorophenyl)-N-isopropyl-carbamoyl]-5-(4H)-tetrazolinone.

9. A compound according to claim 1, wherein such compound is 1-(2-chloro-2-cyclopenten-1-yl)-4-[N-(4-fluorophenyl)-N-isopropyl-carbamoyl]-5-(4H)-tetrazolinone.

10. A herbicidal composition comprising a herbicidally effective amount of a compound according to claim 1 and a diluent.

11. A method of combatting unwanted vegetation which comprises applying to such vegetation or to a locus from which it is desired to exclude such vegetation a herbicidally effective amount of a compound according to claim 1 and a diluent.

12. The method according to claim 11, wherein such compound is 1-(2-chlorocyclohexen-1-yl)-4-(N,N-diethyl-carbamoyl)-5-(4H)-tetrazolinone, 1-(cyclohexen-1-yl)-4-(N-phenyl-N-isopropyl-carbamoyl)-5-(4H)-tetrazolinone, 1-(cyclohexen-1-yl)-4-[N-(4-methylphenyl)-N-isopropyl-carbamoyl]-5-(4H) -tetrazolinone, 1-(2-chlorocyclopenten-1-yl)-4-(N-phenyl-N-isopropyl-carbamoyl)-5-(4H) -tetrazolinone, 1-(2-chlorocyclopenten-1-yl)-4-[N-(4-fluorophenyl)-N-isopropyl-carbamoyl]-5-(4H) -tetrazolinone, or 1-(2-chloro-2-cyclopenten-1-yl)-4-[N-(4-fluorophenyl)-N-isopropyl-carbamoyl]-5-(4H)-tetrazolinone.

13. A compound of the formula

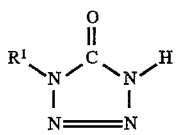

wherein
$R^1$ is cycloalkenyl optionally substituted by halogen or $C_{1-4}$ alkyl, or bicycloalkenyl optionally substituted by halogen or $C_{1-4}$ alkyl.

14. A compound according to claim 13, wherein $R^1$ is $C_{3-8}$ cycloalkenyl optionally substituted by halogen or $C_{1-4}$ alkyl, or $C_{6-8}$ bicycloalkenyl optionally substituted by halogen or $C_{1-4}$ alkyl.

15. A compound according to claim 13, wherein $R^1$ is $C_{5-8}$ cycloalkenyl optionally substituted by fluorine, chlorine, bromine or methyl, or $C_{6-8}$ bicyloalkenyl optionally substituted by fluorine, chlorine, bromine or methyl.

* * * * *